United States Patent [19]

Spence et al.

[11] Patent Number: 4,756,949
[45] Date of Patent: Jul. 12, 1988

[54] METHOD FOR PRODUCING PAD STRUCTURES WITH VISCOELASTIC CORES AND ARTICLE SO MADE

[75] Inventors: Wayman R. Spence, Crawford; Peter Gardiner, Mineral Wells, both of Tex.

[73] Assignee: Kimberly-Clark Corporation, Neenah, Wis.

[21] Appl. No.: 676,090

[22] Filed: Nov. 29, 1984

[51] Int. Cl.[4] .......................... B32B 3/26; B32B 1/00; B32B 31/00
[52] U.S. Cl. ...................................... 428/159; 156/60; 156/303.1; 428/68; 428/314.4; 428/319.7
[58] Field of Search ............... 428/304.4, 314.4, 314.8, 428/319.7, 68, 159; 156/60, 303.1

[56] References Cited

U.S. PATENT DOCUMENTS

| | | | |
|---|---|---|---|
| 3,394,210 | 7/1968 | Franze | 428/304.4 |
| 3,574,021 | 4/1971 | Van Buskirk | 428/319.7 |
| 3,928,704 | 12/1975 | Heidingsfeld et al. | 428/304.4 |
| 4,174,420 | 11/1979 | Anolick et al. | 428/304.4 |

FOREIGN PATENT DOCUMENTS

| | | | |
|---|---|---|---|
| 737431 | 6/1966 | Canada | 428/319.7 |
| 2137194 | 12/1972 | France | 428/319.7 |
| 24951 | 2/1979 | Japan | 428/319.7 |

OTHER PUBLICATIONS

Modern Plastics Encyclopedia, vol. 50, No. 10A, 1973–1974, pp. 107, 108, 113.

*Primary Examiner*—William J. Van Balen
*Attorney, Agent, or Firm*—Donald L. Traut; Jeremiah J. Duggan

[57] ABSTRACT

In accordance with the invention, compositions of matter are provided for forming visco-elastic materials to simulate the physical feel of natural human soft tissue, such as fat or breast tissue. The compositions preferred are formed from a major portion of plasticizer and a minor portion of a resin. In a preferred embodiment, about 1100 parts by weight of a dialkyl phthalate plasticizer are thoroughly mixed with about 100 parts by weight of a polyvinyl chloride resin at an elevated temperature to form the visco-elastic material of the present invention. Included in the preferred composition are minor amounts of an epoxidized soybean oil stabilizer and a metallic salt stabilizer. A method is provided for producing visco-elastic materials and for producing pad structures comprising, preferably, an outer unattached covering of an elastic closed cell neoprene material and a core of said visco-elastic material.

11 Claims, No Drawings

METHOD FOR PRODUCING PAD STRUCTURES WITH VISCOELASTIC CORES AND ARTICLE SO MADE

TECHNICAL FIELD

In one aspect, this invention relates to visco-elastic materials which can be employed as core materials in pads to provide the physical feel of natural soft tissue. The visco-elastic core materials provide such characteristics to pad structures because of their ability to flow or deform under forces greater than gravity, with sufficient elasticity to resume their original shape upon removal of such force.

In another aspect, the invention relates to visco-elastic materials prepared from a major portion of a plasticizer, a minor portion of a resin compatible therewith, and, preferably, stabilizing agents. A still further aspect of the present invention relates to methods by which such materials can be prepared.

Another aspect of the present invention relates to the production of pad structures for protecting parts of the human body from pressure, shearing, friction, vibration, shock and rapid temperature changes, and for simulating the physical feel of natural soft human tissue.

BACKGROUND ART

Various plastic core materials for pads, including for example foamed plastic materials, are well known in the art. These materials, as well as many other conventional padding materials can effectively reduce shock and friction forces imparted to body parts, but the differences in physical properties between such materials and natural soft tissues still allow for transfer of such forces to the user of such prior art pads. For example, athletes such as bicyclists and runners suffer injury from the normal pressure, shearing, friction, and shock that accompany their activities. Blisters are caused on an athlete's feet from exposure to friction occasioned by the foot rubbing against the interior of his shoe. Athletic socks are not capable of absorbing friction, nor can they absorb the shocks experienced by feet occasioned by vigorous exercise. Additionally, bicyclists and sailors also suffer blistered hands even when wearing gloves. Existing plastic padding materials, which can comprise a mixture of about four parts by weight resin with about one part by weight plasticizer, are too rigid and inelastic to prevent slippage between the human foot, buttocks or hand in a shoe, seat or glove, and hence cannot completely eliminate blistering.

Accordingly, a need exists for a highly elastic plastic to conform to the shape of an athlete's body part to protect an athlete against injury caused by pressure, shearing, friction, vibration, and shock occasioned by his athletic activities. Similar needs exist with regard to invalids or persons subject to a period of immobility wherein certain body parts are subject to continuous or prolonged surface contact. Furthermore, a need exists for a material that is highly plastic, and simulates properties of natural soft tissue.

SUMMARY OF THE INVENTION

Visco-elastic materials, especially useful for simulating the characteristics of natural soft tissue when used as the core of pads are provided by preparing a thick solution formed from a major portion of material normally used as a plasticizer with a minor proportion of a resin material compatible therewith. The material can be characterized as either a highly plasticized resin or a plasticizing material thickened with a minor portion of resin. Generally a plasticizer:resin ratio of at least about 10:1 is preferred although for some applications 8:1 can be employed. Stabilizers, i.e. materials which enhance the ability of the mixture to resist degradation can also be employed.

To produce the material, special process steps should be followed in order to insure production of a homogeneous material wherein resin and plasticizer are present in the physical form of a suspension. Preferably, a resin concentrate is prepared by combining the total resin to be employed with a minor portion of the total plasticizer to be used. This resin concentrate is then further diluted by addition of the remaining major portion of a plasticizer.

In a preferred form, the visco-elastic materials of the present invention are prepared using a dialkyl phthalate plasticizer material in combination with a compatible PVC resin. The material is prepared by first forming a resin concentrate at temperatures higher than the gel temperature of the resin and then admixing the concentrate with the major portion of plasticizer to be employed.

The above described visco-elastic materials, when employed as the core of a pad closely simulate the characteristics of natural soft tissue. The outer covering is preferably elastic enough to allow for both horizontal and lateral movement with pressure, and sufficiently flexible so as not to constrain the deformation of the core. Pads formed from an outer covering and a core of the above described visco-elastic materials closely resemble the characteristics of natural tissue in that they will flow or deform under forces greater than those of gravity, but will return to their original shape once the force is removed. The term "pad" as used herein encompasses structures having an outer covering and an inner core of the described visco-elastic materials, whether such structures are intended for use as shields against shock or blistering, such as in bicycle seats, gloves, seat cushions, and shoe inserts, for example, or for use as a prosthetic device, for example a breast prosthesis.

Particularly preferred pad structures employ a core of a visco-elastic material having a major portion of plasticizer and a minor portion of resin with an unattached outer covering of an elastic closed cell neoprene material. Such pads exhibit excellent wear characteristics and provide the physical properties of soft natural tissue. The combination of this type of covering with the visco-elastic core also provide a product which will not exude or otherwise degrade after unacceptably short periods of time.

DETAILED DESCRIPTION

The visco-elastic materials of the present invention can be described as a polymeric solution comprising, in major portion, a plasticizer and in minor portion, a resin. Those skilled in the art will recognize that many plasticizer/resin combinations are possible and that each plasticizer must be chosen with regard to its characteristics when combined with each resin. Suitable resins are those providing low viscosity, high molecular weight, relatively uniform particle size and, of course, compatibility with a plasticizer, both as a finished product and as regards the ability to admix homogeneously therewith during processing. PVC resins provide these characteristics and are preferred. Particularly preferred are PVC resins having specific gravities of approximately 1.4 g/cc. The most preferred PVC resins are those having a specific gravity of about 1.4, are high in molecular weight and have a relative viscosity (1% in cyclo-hexanone at 25° C.) of about 2.85. Such resins are classified as D5-2$\overline{2}$ (ASTM D-1755). PVC resins having these characteristics have excellent compatibility with dialkyl phthalate and impart improved strength and resistance to exudation to the resulting visco-elastic materials.

The plasticizers, as noted above, must be chosen with regard to the particular resin employed. It has been noted that with respect to the resin/plasticizer combinations useful in producing the visco-elastic materials of the present invention one gauge of compatibility is the greasiness of the feel of the final mixture of the two materials. In general, the more greasy the final materials are to the touch, the less compatible are the resin and plasticizer. Preferred plasticizers include dialkyl phthalates. These materials have low volatility, high stability, low melt viscosity, good processability and compatibility with PVC resins. In particular dialkyl phthalate wherein the alkyl groups are mixed $C_7$, $C_9$, and $C_{11}$ and are predominantly linear are preferred. Particularly preferred is n-Heptyln-nonyln-undecyl phthalate with a molecular weight of 414 and a boiling point of about 485.5° F. Visco-elastic materials can be prepared from the resin and plasticizer components alone. When PVC and dialkyl phthalate are employed the preferred component ratios are approximately 11 parts plasticizer to 1 part resin, by weight.

In addition to the plasticizer and resin components, the preferred visco-elastic materials of the present invention also include stabilizers. As used herein, the term "stabilizer" refers to any additive to plasticized resin mixtures which tends to impart resistance to degradation either during processing of the material or in the formed material itself. Such stabilizers must, of course, be chosen with regard to the particular plasticizer/resin system, but should be chosen with toxicity and skin irritation properties in mind in accordance with the end use of the product. When the above described dialkyl phthalate plasticizer/PVC resin combination is employed, the preferred stabilizers are a combination of an epoxy based stabilizer and a metallic salt based stabilizer. In particular, epoxidized soy oil (or linseed or other vegetable oil) and Ba Zn phenate or Ca Zn phenate stabilizers are preferred. In a dialkyl phthalate/PVC system, these two preferred stabilizers, while not strictly necessary in the end product, have been found to provide advantages during processing, apparently by preventing degradation during heating and mixing procedures.

The preferred method for producing pad structures from visco-elastic materials includes preparation of a resin concentrate, addition of plasticizer and colorant to the resin concentrate, and delivery of the material to appropriate molds.

While forming a resin concentrate is not required the most preferred process includes such a step. Basically the resin concentrate is prepared by employing heat and admixing all of the resin to be used with a minor amount of the total plasticizer to be employed.

The above described resin concentrate is then added to the major portion of plasticizer to be employed in the batch. Preferably, plasticizer is placed in an open mixing container and the resin concentrate is added thereto with mixing. The preferred ratio of plasticizer to resin concentrate is about 4:1 by weight. Conventional colorants can be added to the visco-elastic material at this stage to provide whatever colors might be aesthetically desirable.

The visco-elastic material can be delivered to holding vats which are fitted with stirring means and heat sources so as to provide continuous agitation and heat to the formed visco-elastic material. Delivery of the material to molds to form the cores of pad structures for any of the various uses disclosed above can be done in a variety of ways, but preferably can be accomplished using a heated extruder means which increases temperature of the material as it is delivered from the holding vat through the extruder into the molds. Upon cooling the visco-elastic material can be removed from the molds.

The outer covering of the pad structures is not affixed by chemical bonding to the inner core of visco-elastic material. The core of visco-elastic material, enveloped in a loose cover of flexible material, provides a unique combination of the physical feel of natural soft tissue with durability and resistance to movement of the visco-elastic material through the outer covering. The preferred outer covering material is an elastic closed cell neoprene material with a tricot outer layer.

A particularly preferred visco-elastic material can be produced from a minor portion of PVC resin and a major portion of a dialkyl phthalate plasticizer. For example, a resin concentrate can be prepared as follows: First, about 41 parts by weight of dialkyl phthalate plasticizer, is pumped into a mixing tank. To the dialkyl phthalate is added about 5 parts by weight of an epoxidized soybean oil stabilizer and about 6 parts by weight of a metallic salt stabilizer. The preferred epoxidized soybean oil has a commercial name of "Interstab Plastoflex 2307," and can be purchased from John Watson of Dallas, Tex. The preferred metallic salt stabilizer is Ba Zn phenate, which has the trade name of "Synpron 940" and can be purchased from Synthetic Products of Cleveland, Ohio. To this mixture is added approximately 100 parts by weight of PVC resin. The resin concentrate is prepared by heat and mixing with addition of plasticizer until the ratio of plasticizer to resin is about 150:100.

About 4 parts by weight of dialkyl phthalate plasticizer, is pumped into a large galvanized open vat. To this is added about one part by weight of resin concentrate. At 25° C. the plasticizer has a specific gravity of about 0.97 and the resin concentrate has a specific gravity of about 1.15. Coloring agents can then be added to the tank. The diakyl phthalate plasticizer, resin concentrate, and coloring are thoroughly mixed. This mixture is then pumped into a holding vat which is continually stirred and heated to maintain the mixture at a temperature of from about 100° F. to about 115° F. From the holding vat, the mixture can be extruded into a mold. The extruder has an oil heater, which is set to about 500° . During the extrusion process the visco-elastic material should enter the extruder at a temperature of from about 100° F. to about 115° F. and should exit the extruder into the mold at a temperature of from about 330° F. to about 350° F.

The molded visco-elastic material is then covered with an unattached envelope of elastic closed-cell neoprene material with a tricot layer such as that sold under the tradename Rubatex, No. 301 by Rubatex Inc., Bedford Va. The pads can be in the shape of final use, for example a bicycle seat or can be of a shape suitable for incorporation into another structure, such as the palm of a glove.

The following example is provided, not to limit the invention, but rather to further aid one skilled in the art in understanding the process by which the visco-elastic materials of the present invention can be prepared.

EXAMPLE

Approximately 275 pounds of the dialkyl phthalate plasticizer are delivered to a 300 gallon mixing tank. To the plasticizer is added 33 pounds of epoxidized soybean oil (Interstab Plastoflex 2307) and about 40 pounds of Ba Zn phenate (Synpron 940). To this mixture is added thirteen 50 pound bags (a total of 650 pounds) of polyvinyl chloride resin. A resin concentrate is prepared with heat, mixing, and addition of plasticizer until a total of about 975 pounds of plasticizer is present in the resin concentrate.

Next approximately 1,024 pounds of dialkyl phthalate is pumped into a large open vat. The material has a specific gravity of about 0.97 at 25° C. To the plasticizer material is added 256 pounds of the resin concentrate formed as described above. A tan colored master batch of coloring agents (prepared by previously admixing desired proportions of white, yellow and red coloring) is added to the tank and the resin concentrate, plasticizer, and colorant are thoroughly admixed with the mixing blade attached to an electric drill. The material is then transferred to a holding vat which is continually stirred and heated to a constant temperature of approximately 115° F. The mixture is then pumped through an extruder into the appropriate mold to make the desired item. The extruder has an oil heater which is set at 500° F. and heats the incoming liquid to an exit temperature of approximately 350° F.

The material is delivered to a bicycle seat mold where it is allowed to cool. A covering of Rubatex #301, a closed cell neoprene with a tricot layer, is then fitted over the visco-elastic core so as to envelope it without chemical bonding of the covering to the core.

While the invention has been described above with respect to its preferred embodiments, it will be understood that the invention is capable of numerous rearrangements, modifications and alterations and all such arrangements, modifications and alterations are intended to be within the scope of the appended claims.

We claim:
1. A pad structure comprising an unattached outer covering of an elastic closed-cell neoprene material and a core of visco-elastic material, said core imparting to the pad structure the physical feel of natural soft tissue characterized by an ability to flow under forces exceeding gravity with sufficient elasticity to resume its original shape upon removal of such force, said core material comprising, in a major portion, a plasticizer and in minor portion a resin material compatible with said plasticizer, said ratio of plasticizer to resin in said visco-elastic material is at least about 10:1 by weight.

2. The pad structure of claim 1 wherein the resin of said visco-elastic material is a PVC resin.

3. The pad structure of claim 2 wherein said plasticizer is a dialkyl phthalate.

4. The pad structure of claim 3 wherein the ratio of dialkyl phthalate to PVC resin is about 11:1 by weight.

5. The pad structure of claim 1 wherein said core and outer covering is configured to support the human buttocks.

6. The pad structure of claim 1 wherein said core is incorporated into the palm of a glove.

7. The pad structure of claim 1 wherein said outer covering and core form a portion of a seat cushion.

8. The method for forming pad structures having visco-elastic core materials comprising:
    (a) forming a resin concentrate by admixing all of the resin to be employed with a minor portion of the total plasticizer to be employed;
    (b) admixing said resin concentrate with the remaining plasticizer to be employed to achieve a plasticizer:resin ratio of at least about 10:1 by weight;
    (c) heating the resulting visco-elastic material and extruding same into molds of desired shapes; and
    (d) covering said visco-elastic molded shapes with an unattached outer covering of elastic closed cell neoprene material.

9. The method of claim 8 wherein said visco-elastic material is produced from a PVC resin and a dialkyl phthalate plasticizer.

10. The method of claim 9 wherein said visco-elastic materials are heated to a temperature of from about 330° to about 350° F. during extrusion into the molds.

11. The method of claim 9 wherein during formation of the resin concentrate a combination of epoxy stabilizers and metallic salt stabilizers are added.

* * * * *